(12) United States Patent
Pilgaonkar et al.

(10) Patent No.: US 9,295,643 B2
(45) Date of Patent: Mar. 29, 2016

(54) **FIBER RICH FRACTION OF *TRIGONELLA FOENUM-GRACEUM* SEEDS AND ITS USE AS A PHARMACEUTICAL EXCIPIENT**

(76) Inventors: Pratibha S. Pilgaonkar, Mumbai (IN);
Maharukh T. Rustomjee, Mumbai (IN);
Anilkumar S. Gandhi, Mumbai (IN);
Vinderjit Sarjit Bhumra, Mumbai (IN)

( * ) Notice: Subject to any disclaimer, the term of this patent is extended or adjusted under 35 U.S.C. 154(b) by 2162 days.

(21) Appl. No.: 10/945,938

(22) Filed: Sep. 21, 2004

(65) Prior Publication Data

US 2005/0084549 A1  Apr. 21, 2005

Related U.S. Application Data

(63) Continuation-in-part of application No. 10/439,161, filed on May 12, 2003, now abandoned.

(51) Int. Cl.
| | |
|---|---|
| *A61K 36/00* | (2006.01) |
| *A61K 9/00* | (2006.01) |
| *A61K 9/16* | (2006.01) |
| *A61K 9/20* | (2006.01) |
| *A61K 9/28* | (2006.01) |
| *A61K 9/70* | (2006.01) |
| *A61K 47/46* | (2006.01) |

(52) U.S. Cl.
CPC .............. *A61K 9/006* (2013.01); *A61K 9/0014* (2013.01); *A61K 9/0095* (2013.01); *A61K 9/1664* (2013.01); *A61K 9/2068* (2013.01); *A61K 9/288* (2013.01); *A61K 9/7007* (2013.01); *A61K 47/46* (2013.01)

(58) Field of Classification Search
CPC ...................................................... A61K 36/48
See application file for complete search history.

(56) References Cited

U.S. PATENT DOCUMENTS

| | | | |
|---|---|---|---|
| 5,288,618 | A | 2/1994 | Hardin et al. |
| 5,658,571 | A | 8/1997 | Gopalan et al. |
| 5,847,109 | A | 12/1998 | Garti et al. |
| 5,997,877 | A | 12/1999 | Chang |
| 6,063,402 | A | 5/2000 | Gebert et al. |
| 6,495,175 | B2 | 12/2002 | Rao et al. |
| 2001/0024665 | A1 | 9/2001 | Rao et al. |

FOREIGN PATENT DOCUMENTS

| | | |
|---|---|---|
| JP | 2001025265 | 1/2001 |
| WO | 99/25197 | 5/1999 |
| WO | 01/28673 | 4/2001 |
| WO | WO 0174371 A1 * | 10/2001 |

OTHER PUBLICATIONS

Fernández-Garcia, E et al. A. Lebensm Unters Forsch A (199&), 204: 433-437. Fortication of sweetened plain yogurt with insoluble dietary fiber.*
Sharma, R. D. Nutrition Research (1986), 6: 1353-1364. Effect of fenugreek seeds and leaves on blood glucose and serum insulin responses in human subjects.*
Brummer, Yet al. Food Hydrocolloids; 17 (May 23, 2003): 229-236. Extraction, purificaton and physiochemical characterization of fenugreek gum.*
Ribes, G et al. Ann Nutr Metab. 1984;28(1):37-43. Effects of fenugreek seeds on endocrine pancreatic secretions in dogs.*
Brummer, Y et al. Food Hydrocolloids; 17 (May 23, 2003): 229-236. Extraction, purificaton and physiochemical characterization of fenugreek gum.*
Ribes, G et al. Proceedings of the Society for Experimental Biology and Medicines; 182: 159-166 (1986). Antidiabetic effects of subfrations from fenugreek seeds in diabetic dogs.*
Ribes et al., "Effects of Fenugreek Seeds on Endocrine Pancreatic Secretions in Dogs," Ann. Nutr. Metab. 28: 37-43 (1984).
Petropoulos G. A., "Fenugreek The genus *Trigonella*," Taylor and Francis Publication, pp. 9 (2002).
Al-Habori M. A. et al., "Fenugreek the genus *Trigonella*," Taylor and Francis Publication, pp. 162 (2002).
Evans A. J. et al., "Relationship Between Structure and Function of Dietary Fiber: A Comparative Study of the Effects of Three Galactomannans on Cholesterol metabolism in the rat," British J. Nut, vol. 68, pp. 217-229 (1992).
Ribes G. et al., "Hypocholesterolaemic and hypotriglyceridaemic effects of subfractions from fenugreek seeds in alloxan diabetic dogs," Phytotherapy Research, vol. 1 (1), pp. 38-43 (1987).
Remingston: The Science and Practice of Pharmacy, vol. 1, pp. 868 (2002).

* cited by examiner

*Primary Examiner* — Qiuwen Mi
(74) *Attorney, Agent, or Firm* — Blank Rome LLP

(57) ABSTRACT

A solvent free process of obtaining an insoluble fiber rich fraction from *Trigonella Foenum-graceum* seeds is disclosed. The multifunctional fiber rich fraction (FRF) and highly purified FRF are useful as excipients for pharmaceutical dosage forms for various routes of administration. These excipients can be used as binder, disintegrant, filler, dispersing agent, coating agent, film forming agent, thickener and the like, for preparation of variety of dosage forms. FRF and highly purified FRF can also be used in a controlled release, targeted release and other specialized delivery systems, as well as in food and cosmetics formulation.

8 Claims, 4 Drawing Sheets

Trigonella Foenum-graceum Seeds selected based on physical properties such as dimensions, swelling factor etc.

↓

Size reduction using a comminuting mill with differential speed and screen

↓

Fractionation carried out using a sieve with a suitable mesh size

→ Yellow embryo portion (discarded)

↓

Translucent Fraction relatively rich in Fiber content

↓

Process for size reduction repeated several times till the desired product characteristics achieved (However the product still may contain some amount of yellow embryo)

↓

Further separation is carried out based on the relative densities of the embryo and Fiber rich fraction → Yellow embryo portion (discarded)

↓

Fraction thus obtained is further purified

↓

Fiber Rich Fraction (FRF) with desired properties (Swelling factor, viscosity, gel strength etc)

FIG. 2

FIBER RICH FRACTION OF *TRIGONELLA FOENUM-GRACEUM* SEEDS AND ITS USE AS A PHARMACEUTICAL EXCIPIENT

RELATED APPLICATIONS

This application is a continuation-in-part application of U.S. application Ser. No. 10/439,161, filed May 12, 2003 now abandoned, which is hereby incorporated by reference in its entirety.

FIELD OF THE INVENTION

The present invention generally relates to a solvent free process of obtaining an insoluble fiber rich fraction from *Trigonella Foenum-graceum* seeds. The invention further relates to the fraction obtained from *Trigonella Foenum-graceum* seeds, having at least 50% of dietary fiber with a ratio of insoluble dietary fiber to soluble dietary fiber greater than 0.8 and a protein content not more than 10 weight % with a viscosity greater than 10000 cps at 2% w/v concentration. The invention also relates to the process of purifying the fiber rich fraction to obtain a highly purified fiber rich fraction. The invention further discloses use of fibre rich fraction (FRF in short) or highly purified FRF as a pharmaceutical excipient in various pharmaceutical dosage forms.

BACKGROUND OF THE INVENTION

*Trigonella Foenum-graceum* commonly known as Fenugreek is an herbaceous plant of the leguminous family and is native to Western Asia, from where it has spread widely over Europe, the Mediterranean and rest of Asia. It is one of the oldest cultivated plants and through the ages has found wide applications as a food, a food additive and as a traditional medicine in every region wherein it has been cultivated. The leaves and both the ripe and unripe seeds of *Trigonella Foenum-graceum* are used as vegetables. The seeds also function as a food preservative and are added to pickles, chutneys, and other similar food products. (Petropoulos G. A, "Fenugreek The genus *Trigonella*", 2002, Taylor and Francis Publication, pp-9)

The ripe seeds have numerous applications in the traditional medicine system of India. Fenugreek has been used in treating colic flatulence, dysentery, diarrhea, dyspepsia with loss of appetite, chronic cough, dropsy, enlargement of liver and spleen, rickets, gout and diabetes. The seed is stated to be a tonic. It is also used in post-natal cure and to increase lactation in nursing mothers. (Al-Habori M. A et al "Fenugreek the genus *Trigonella*", 2002, Taylor and Francis Publication, pp-162)

The different parts of Fenugreek seeds are indicated in FIG. 1. Fenugreek seeds are surrounded by the seed coat or the Testa (designated as 3 in FIG. 1). The seed coat is separated from the embryo (designated as 1 in FIG. 1) by a well-developed endosperm (designated as 2 in FIG. 1), which is the principal storage organ. In mature seeds the majority of the endosperm cells are nonliving, the cytoplasmic content of which are occluded by the store reserves viz galactomannan. Fenugreek seed contains a large number of compounds such as volatile oil, fixed oils, proteins, carbohydrates, dietary fibers, hemicellulose, galactomannans, cellulose, saponins, resins, pigments, vitamins, minerals and others.

Typical analysis results of fenugreek seeds are documented in the table 1 hereunder:

TABLE 1

Typical analysis of fenugreek seeds

| | CONSTITUENT | PERCENTAGE |
|---|---|---|
| 1. | MOISTURE | 9.0 |
| 2. | ASH | 3.2 |
| 3. | LIPIDS | 7.0 |
| 4. | PROTEINS | 26.0 |
| 5. | STARCH | 1.6 |
| 6. | FIBER | 48.0 |
| | Mucilage | 20.0 |
| | Hemicelluloses | 17.3 |
| | Cellulose | 8.2 |
| | Lignin | 2.5 |
| 7. | SAPONIN | 4.8 |
| 8. | TRIGONELLINE | 0.37 |

(Source: THE WEALTH OF INDIA, CSIR GOVT. OF INDIA PUBLICATION.)

Various seed components of *Trigonella Foenum-graceum* along with the dietary fiber have an important role in the treatment and management of several disorders such as obesity, coronary heart disease, diabetes, piles, fissures, chronic constipation and diverticulitis. The saponins are reported to contain active components that are anti-carcinogenic, anti-microbial and/or anti-oxidant.

The dietary fiber is the non-absorbable and indigestible fibrous portion, which is not assimilated by the body and is non-caloric and has substantially no nutrition value. It includes both soluble and insoluble fibers. Insoluble dietary fibers primarily comprise cellulose, lignin and some hemicelluloses; while soluble dietary fiber comprises pectin, gums and some hemicelluloses. (Evans A. J. et al, British J. Nut, 68(i), 1992, 217-229).

Owing to the versatile functionality of the various seed components of Fenugreek, attempts have been made to isolate these components using various processes. These processes primarily make use of organic solvents for extraction of the components. Majority of prior art teaches various processes of isolating a fraction that is rich in soluble dietary fibers. The particular emphasis for isolation of soluble dietary fiber is due to the physiological action of soluble dietary fibers, which makes them useful in the treatment of diabetes as well as obesity and other conditions (Sharma R. D., Eur. J. Clin. Nutr., Vol. 44, 1990, pp 301). Isolation of dietary fibers chiefly insoluble dietary fibers to arrive at a insoluble fiber rich fraction is of particular significance for the purpose of the present invention more particularly in establishing their hitherto untapped uses as pharmaceutical excipient.

Organic solvent-based methods for isolating soluble dietary fiber of the *Trigonella Foenum-graceum* seeds are known in the art.

Peter CHANG, in U.S. Pat. No. 5,997,877, discloses a process for isolation of oleoresins, saponins and a soluble dietary fiber. The process comprises of tempering fenugreek seeds to moisture level of 16-22%, followed by flaking using roller mill and sieving to separate the seed coat from cotyledon. The separated seed coat portion is treated with hot water for several hours, centrifuged and precipitated using a polar alcohol. Precipitate thus obtained is rich in soluble dietary fiber, which is further washed and dried.

Tempering/flaking before extraction is carried out to increase the extraction recovery ratio and decrease the contact times. To achieve proper tempering, seeds are mixed with water and kept aside for 24 hrs prior to flaking. The product so obtained is rich in soluble dietary fibers.

Flaking, which is an essential step for separation of seed coat from cotyledon in the disclosed process will not occur at ambient moisture content of fenugreek seeds. This makes the isolation process time intensive since tempering requires initial determination of the moisture content of the seed, followed by addition of a fixed quantity of water to achieve the desired moisture level uniformly. This not only increases the time of extraction process but also some times lead to hydrolysis of the lipids leading to discoloration of the final product as pointed out in U.S. Pat. No. 6,495,175.

In another embodiment of the same patent fenugreek seeds are treated with polar alcohols at high temperatures to isolate the oleoresin component prior to isolation of soluble dietary fiber; however the process may lead to loss of some amount of dietary fibers (Rao G. B. et al US patent application 20010024665A1). Dietary fibers are also further isolated by heating the fenugreek flakes with water at 60 degrees for 4 hrs which may affect the quality of the final product as well as the viscosity of the dietary fiber obtained.

Rao G. B. et al in U.S. Pat. No. 6,495,175 and US patent application 20010024665A1 describe a two step solvent extraction process wherein first extraction isolates fixed oils and second extraction isolates oleoresins leaving the light yellow to light brown dietary fiber. All of the above processes described in the prior art use high temperature, solvents and specialized extractor that makes the process very difficult on the commercial scale. Since the embryo is not separated from the dietary fiber at the time of grinding or isolation the fibers obtained have higher protein content, which is not a desirable attribute for use as a pharmaceutical excipient. The process disclosed in U.S. Pat. No. 5,658,571 by Gopalan et al also involves a special kind of reactor and solvents and has similar disadvantages.

Osband M. E. describes another solvent-based extraction process in PCT application WO9925197. The process results in a product having a high amount of protein (about 20-40%), which not only reduces the amount of dietary fiber content in the end product but also is undesirable for it to act as a pharmaceutical excipient.

BOURRET E., PCT application WO/0174371AI disclosed a method of using organic solvents to obtain *Trigonella Foenum-graceum* mucilage in the form of flour with grain size distribution less than 100 µm, consisting mannose, galactose, glucose, arabinose, xylose, rhamnose, D-galacturonic acid, galactomannans, and proteins. The key feature of the invention is pulverization of non-lipid fraction of fenugreek seed at sub zero temperatures (−195 degrees) to improve the solubility of non-lipid fraction of fenugreek seed in the extracting solvent. This requires a specialized facility to carry out such an operation and thus increases the cost of isolation of the dietary fiber.

U.S. Pat. No. 5,847,109 by Garti N. et al describes process of isolation involving use of organic solvents and high temperatures as well as specialized equipment for isolation of various components from fenugreek seed. Dietary fibers are also extracted using the same equipment and the same seeds following numerous treatments with different solvents. The process also involves treatment with polar alcohols, which may reduce the yield of the dietary fiber. The process yields dietary fibers with high protein content and to further reduce the protein content chromatographic techniques are suggested which are difficult and expensive to carry out at commercial scale.

PCT application WO 0128673AI describes the manufacture or isolation of galactomannans using various organic solvents, and the use of such galactomannans.

The prior art processes of isolation, as seen above are based on organic solvents, which may leave toxic residues and may pose problems during large scale handling. Moreover the time and technique intensive processes are cumbersome and costly at the same time are unable to result in desired quality dietary fiber.

Mechanical process of isolation has been described in the Japanese patent application JP 2001025265. The process involves special equipment comprising of a cylindrical vessel made up of metal net with 150 mesh screen and rotary wings for separating the endosperm. The seed of fenugreek are very difficult to pulverize and therefore keeping a 150 mesh screen means pulverization for a prolonged period leading to generation of local hot spots which may affect the properties of the final product. This process thus needs specialized equipment, and also there is a possibility that characteristics of the final product may be altered.

Prior art review shows attempts made to isolate the dietary fibers predominantly containing insoluble dietary fiber in higher purity are largely unsuccessful owing to non-specific isolation techniques, use of costly and specialized equipments, use of organic solvents for extraction and energy intensive methods. Moreover isolation of the dietary fibers was targeted more particularly to isolation of soluble dietary fibers for their therapeutic use or soluble dietary fibers with high protein content for nutritional purposes.

Prior art does not reveal any processes targeted towards maximizing isolation of insoluble dietary fibers with low protein content and high viscosity that can be used as a pharmaceutical excipient.

Although patents such as U.S. Pat. No. 5,288,618 by Hardin, U.S. Pat. No. 6,039,980 by Baichwal and U.S. Pat. No. 6,063,402 by Gebert describe pharmaceutical applications of galactomannan, none of these applications anticipate use of fenugreek galactomannan-fibers rich fraction as pharmaceutical excipient having high viscosity and binding properties. As a matter of fact, prior art teachings describe fenugreek as less efficient thickening agent (U.S. Pat. No. 5,847,109 and Brumer Y. et al, Food hydrocolloids, vol. 17(3), pp 229, 2003). It is particularly relevant to note that the prior art teaching of fenugreek as less efficient thickening agent undermines the effective use of the seed as pharmaceutical excipient while the present invention aims at providing fenugreek fiber rich fraction as a superior pharmaceutical excipient.

SUMMARY OF THE INVENTION

The instant invention is surprisingly different in that the process described herein leads to a fraction of insoluble and soluble dietary fibers resulting in a product rich in insoluble dietary fiber that has unexpected properties and comparable viscosities to the polymers reported in the literature commonly used as pharmaceutical excipients. This fiber rich fraction also results in a unique chemistry, having not only galactomannan but also celluloses, and hemicellulose, which contribute to the unique properties of the fiber rich fraction as a pharmaceutical excipient. Owing to the unique chemistry, the excipient can also have food and cosmetic applications.

Contrary to the teachings of prior art, the present invention aims at isolation of a fraction of dietary fiber of Fenugreek seed with a ratio of insoluble dietary fiber to soluble dietary fiber greater than 0.8 with a protein content not more than 10% with a viscosity greater than 10000 cps at 2% w/v concentration and its use as pharmaceutical formulation excipient.

The invention also aims at an efficient separation system using grinding and sieving of the fenugreek seeds for isolating fiber rich fraction, in contrast to prior art (U.S. Pat. No. 6,495,175 and US patent application 20010024665A1) which aims only at pulverizing the entire seed which will always contain husk and embryo together, and does not ensure separation of the husk from the embryo as described in the present invention.

It is thus an object of the present invention to provide a solvent free process of obtaining an insoluble fiber rich fraction from *Trigonella Foenum-graceum* seeds.

Another object of the present invention is to provide a solvent free process of obtaining an insoluble fiber rich fraction from *Trigonella Foenum-graceum* seeds that is simple, cost and energy effective and does not use organic solvents or specialized equipments.

Yet another object of the present invention is to provide a insoluble fiber rich fraction from *Trigonella Foenum-graceum* seeds having at least 50% of dietary fiber with a ratio of insoluble dietary fiber to soluble dietary fiber greater than 0.8 and a protein content not more than 10% with a viscosity greater than 10000 cps at 2% w/v concentration.

Yet another object of the present invention is to provide a highly purified insoluble fiber rich fraction obtained by purifying the fiber rich fraction from *Trigonella Foenum-graceum* seeds.

Another object of the present invention is to provide a process for purifying insoluble fiber rich fraction obtained from *Trigonella Foenum-graceum* seeds to obtain a highly pure insoluble fiber rich fraction.

Yet another object of the present invention is to provide the fiber rich fraction and highly purified fiber rich fraction as a multifunctional pharmaceutical excipient employing individually as a release retarding polymer, a disintegrant, a binder, a suspending agent, a gelling agent, a film forming agent, capsule forming agent, a diluent and as a carrier for drug.

Yet another object of the present invention is to provide pharmaceutical compositions containing the fiber rich fraction or the highly purified fiber rich fraction.

Thus according to an aspect of the present invention there is provided a process for producing an insoluble fiber rich fraction from *Trigonella Foenum-graceum* seeds comprising:
providing *Trigonella Foenum-graceum* seeds of predetermined dimensions and swelling factor;
subjecting the seeds to milling to break the seeds to obtain a mixture of embryo and husk in which the embryo breaks in the form of particles;
passing the mixture through a sieve to substantially separate the embryo and the husk, the separated husk fraction contains some embryo portion;
if desired, the separated husk is again subjected to milling and separation so as to ensure that husk fraction contains no more than 20% of embryo.

The embryo content is preferably reduced to a level of no more than 10% and more preferably to a level of no more than 5%.

In yet another aspect of the present invention there is provided an insoluble fiber rich fraction wherein the fiber rich fraction contains from 50% to 80% by weight. preferably from 50% to 75% by weight of dietary fibers in which the ratio of insoluble to soluble dietary fiber is greater than 0.8, preferably 1.2-3.0, insoluble dietary fiber greater than 28% preferably greater than 30%, with a protein content of not more than 10 weight % with a viscosity greater than 10000 cps at 2% w/v concentration.

According to yet another aspect of the present invention there is provided a highly purified insoluble fiber rich fraction obtained from the insoluble fiber rich fraction of the present invention wherein the fraction contains from 50% to 98% by weight. preferably from 50% to 95% by weight of dietary fibers in which the ratio of insoluble to soluble dietary fiber is greater than 0.8, preferably 1.2-3.0, insoluble dietary fiber greater than 30% preferably greater than 32% by weight., with a protein content of not more than 10 weight % with a viscosity greater than 50000 cps at 2% w/v concentration.

In yet another aspect of the present invention there is provided use of the fiber rich fraction and the highly purified fiber rich fraction as pharmaceutical excipients in appropriate amounts so as to be effective as a release-retarding polymer, disintegrant, binder, suspending agent, gelling agent, film forming agent, capsule forming agent and the like.

According to yet another aspect of the present invention there are provided pharmaceutical compositions comprising an active pharmaceutical ingredient and the fiber rich fraction or the highly purified fiber rich fraction as pharmaceutical excipients in appropriate amounts.

BRIEF DESCRIPTION OF THE FIGURES

FIG. 2 demonstrates a representative flow chart for the process of isolation of the fiber rich fraction (FRF).

DETAILED DESCRIPTION

Figure 1:
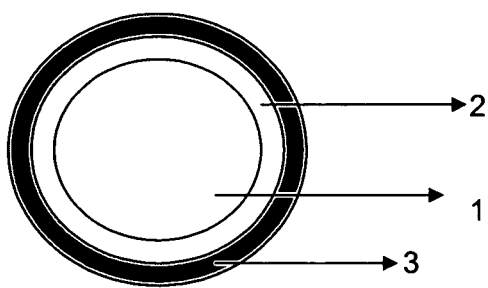
FIG. 1 illustrates a schematic view of the various seed components of *Trigonella Foenum-graceum* or Fenugreek seeds. (1) embryo, (2) endosperm, (3) testa.

A process of obtaining an insoluble fiber rich fraction from *Trigonella Foenum-graceum* seeds without the use of organic solvents or specialized equipments is described herein.

The term "Fiber rich fraction" according to present invention means a fraction containing at least 50% of the dietary fiber and having a viscosity >10,000 cps and is obtained by a physical process of separation of husk from the embryo of the *Trigonella foenum-graceum* seeds.

The term "highly purified Fiber rich fraction" according to present invention means a fraction containing at least 50% of the dietary fiber and having a viscosity of >50,000 cps and is obtained by a purification of fiber rich fraction.

The fiber rich fraction (FRF) is unique in having at least 50% of dietary fibers with a ratio of insoluble dietary fiber to soluble dietary fiber greater than 0.8, with protein content not more than 10 weight % preferably not more than 8 weight % and with a viscosity greater than 10000 cps at 2% w/v concentration. The simple process of manufacture leaves no organic residues or toxic byproducts in the FRF since it does not utilize organic solvents thus making the FRF extraordinarily pure and safe. Due to its purity and lack of organic solvent contamination FRF obtained in the present invention is exceptionally valuable as an excipient in pharmaceutical manufacturing. Also the physical process of the present invention utilizes equipments commonly employed by pharmaceutical industry thereby simplifying scale up and commercialization in comparison with prior art processes using specialized equipments.

The invention at least in part is based on the process of isolation of dietary fiber i.e. FRF from Fenugreek seeds. Furthermore, the instant invention describes the use of the isolated product as a pharmaceutical excipient due to its unique properties.

It is pointed that highly purified fiber rich fraction has identical but superior properties in comparison with fiber rich fraction and any references made herein to the use of fiber rich fraction shall be construed to imply the use of highly purified fiber rich fraction in a similar application.

The fiber rich fraction described in the present invention offers a number of advantages to a pharmaceutical formulation scientist. It is a multifunctional excipient, which can be used for a variety of applications in pharmaceuticals. This excipient can be used as a release retarding polymer, a binder, a suspending agent, a gelling agent, coating agent, a film forming agent, a diluent and as a carrier for drug. It acts as a good release-retarding polymer for drugs with varying solubilities, particularly for highly soluble drugs, which are difficult to formulate in controlled release formulation. It also acts as a good suspending agent. It can be used in all liquid, semisolid and solid dosage forms. It can be formulated for oral, nasal, ocular, urethral, buccal, transmucosal, vaginal, topical or rectal delivery.

Use of "appropriate amounts" of the pharmaceutical excipient herein means, known amounts of the defined excipient that can be readily used as a release retarding polymer, disintegrant, binder, suspending agent, gelling agent, film forming agent, capsule forming agent and the like. These amounts can be readily determined by one of ordinary skill in the art.

It presents no toxicity risks, as it is "GRAS" listed. ("Generally Recognized as Safe" by the United States Food and Drug Administration). It can also be adapted for large-scale production.

The process steps involved in isolation of the fiber rich fraction from the Fenugreek seeds will now be described hereunder in greater details.

The isolation of FRF involves steps such as selection of seeds, sequential milling, separation of embryo and enrichment of FRF by way of density difference. The difference in the brittleness of the embryo and the husk is exploited in an essentially serial and controlled milling process to achieve separation of the embryo from the husk. The embryo is highly brittle and powders easily but the husk is highly elastic and tenacious and very difficult to powder.

The preferred embodiment for carrying out the process steps involved in isolation of the fiber rich fraction from the Fenugreek seeds is illustrated in the flow chart represented by FIG. 2. Each of the process steps is discussed below in detail.
(a) Selection of Seeds:

The first step in the isolation of FRF is the selection of seeds having desired dimensions and swelling factor. Seeds having length between 3.0-6.0 mm, preferably 3.5-4.5 mm and breadth ranging from 1.5-4.0 mm, preferably 2.0-3.5 mm are selected. The swelling factor ranging 0.5-50.0, preferably 3.0-35.0 ml is used in the isolation process.

Moisture content of the fenugreek seeds is also an important parameter. Seeds with a moisture content of greater than 10% are difficult to process as per the instant invention. In such cases the seeds are dried at 60 degrees centigrade to achieve the moisture level of less than 10% and then subsequently employed for isolation of FRF.
(b) Milling:

The selected seeds are treated to isolate the somewhat translucent FRF. As the process of isolation involves physical separation no special care as regard to use of solvents is necessary.

The physical treatment process entails milling the selected Trigonella foenum-graceum seeds in a multimill with hammer forward at fast speed. Any mill such as comminuting mill, hammer mill, which is able to mill-break the Trigonella foenum-graceum seeds can be employed.

Fenugreek seed is known to have central, hard yellow embryo, which is surrounded by husk comprising of corneous endosperm and tenacious testa.

The milling operation results in physical separation of husk from the yellow embryo, to make a mixture of the two components physically together, but no longer physically attached to each other.

The sieve of the multimill is selected in such a way that it does not allow the whole seed to pass through at the same time allows powdered embryo and husk to pass through. Sieve that are used for the invention range from 1.0 mm to 7.0 mm however, preferred sieves are 2.5 mm to 5 mm based on the dimensions of the seeds. Use of very fine sieve may result in unnecessary longer processing times, local heat generation and the properties of the FRF obtained may be compromised.
(c) Separation of Husk from Yellow Embryo:

Separation of husk and the yellow embryo from the physical blend may be carried out by sieving through a sieve ranging from 8# to 80#, preferably 16 # sieve. The fraction passing through the sieve i.e., the yellow embryo-rich fraction is discarded and the fraction retained on the sieve is the fraction relatively rich in husk.
(d) Sequential Milling:

One important aspect of the invention is the sequential milling of Trigonella foenum-graceum seed. Husk thus obtained still contains significant amount of yellow embryo in the physical mix, this mix is therefore again fed into the multimill under similar operating condition to further grind the yellow seed fraction and the process is repeated till the fraction retained on the sieve is rich in the husk fraction (no more than 20% of the yellow embryo). This may take from minimum of 2 to a maximum of 18 passages through the multimill. The process can be automatized wherein the fraction retained on the sieve is automatically added as a feed to the multimill. The sequential milling of Fenugreek seed is an important aspect of the invention.
(e) Enrichment of FRF by Fluidization Using Density Difference:

The fraction thus obtained may still contain about 20% of the yellow embryo and further separation of this is carried out by a process based on the density difference between the husk and the yellow embryo. The process involves fluidization of the physical blend of fraction rich in husk and yellow embryo in a stream of air. As yellow embryo is denser than husk fraction, the husk is blown away during fluidization in a separate chamber whereas the yellow embryo remains in the same chamber. The husk-containing fraction is further sieved through 12# to obtain a fraction that is rich in dietary fiber i.e. Fiber Rich Fraction or FRF. The embryo content in FRF is less than 10%, preferably less than 5%.
(f) Powdering of FRF to Desired Particle Size:

The resulting fraction is Fiber Rich Fraction i.e FRF which can be further milled using a roller mill, grinding mill or any other suitable mill to the desired particle size. Desired particle size as referred herein is any particle size that is suitable for incorporation into a pharmaceutical dosage form. The FRF thus obtained has unique properties resulting from the combination of soluble as well as insoluble dietary fiber.

Analysis of FRF of the Present Invention:

FRF isolated from process of the instant invention was analyzed using standard AOAC methods and the results are indicated in table 2 below:

TABLE 2

(a) Characterization of FRF

| No. | Test | Results (% Weight) |
|---|---|---|
| 1 | Moisture content (AOAC 17th edition 2000, 925.10) | <10% |
| 2 | Total ash (AOAC 17th edition 2000, 923.03) | <5% |
| 3 | Fat (AOAC 17th edition 2000, 984.13) | <5% |
| 4 | Protein (N × 6.25) (AOAC 17th edition 2000, 920.85) | <10% |
| 5 | Dietary fibers (AOAC 17th edition 2000, 991.43) | 50-80% |
|   | Insoluble dietary fiber (ISDF) | 28-70% |
|   | Soluble dietary fiber (SDF) | 10-30% |
|   | ISDF/SDF | >0.8 |
| 6 | Viscosity at 2% w/v Using Brookfield viscometer | >10,000 cps |

The amount of dietary fibers in the FRF obtained by the process of the present invention is 50-80%, preferably 50-75%.

The ratio of insoluble to soluble dietary fiber is greater than 0.8 preferably greater than 1.2, more preferably from 1.2 to 3.0. Protein content in the FRF is not more than 10% preferably not more than 8%.

Highly Purified FRF

The invention further encompasses purifying the fiber rich fraction to obtain a highly purified form of FRF. Purification can be carried out using various solvents, employing the method described by Ribes et al (Ribes G. et al, Phytotherapy research, 1 (1), 1987, 38-43) wherein the aqueous dispersion of FRF could be treated with solvents to get a highly purified FRF rich in galactomannan and other cellulosic components.

Figure 3:
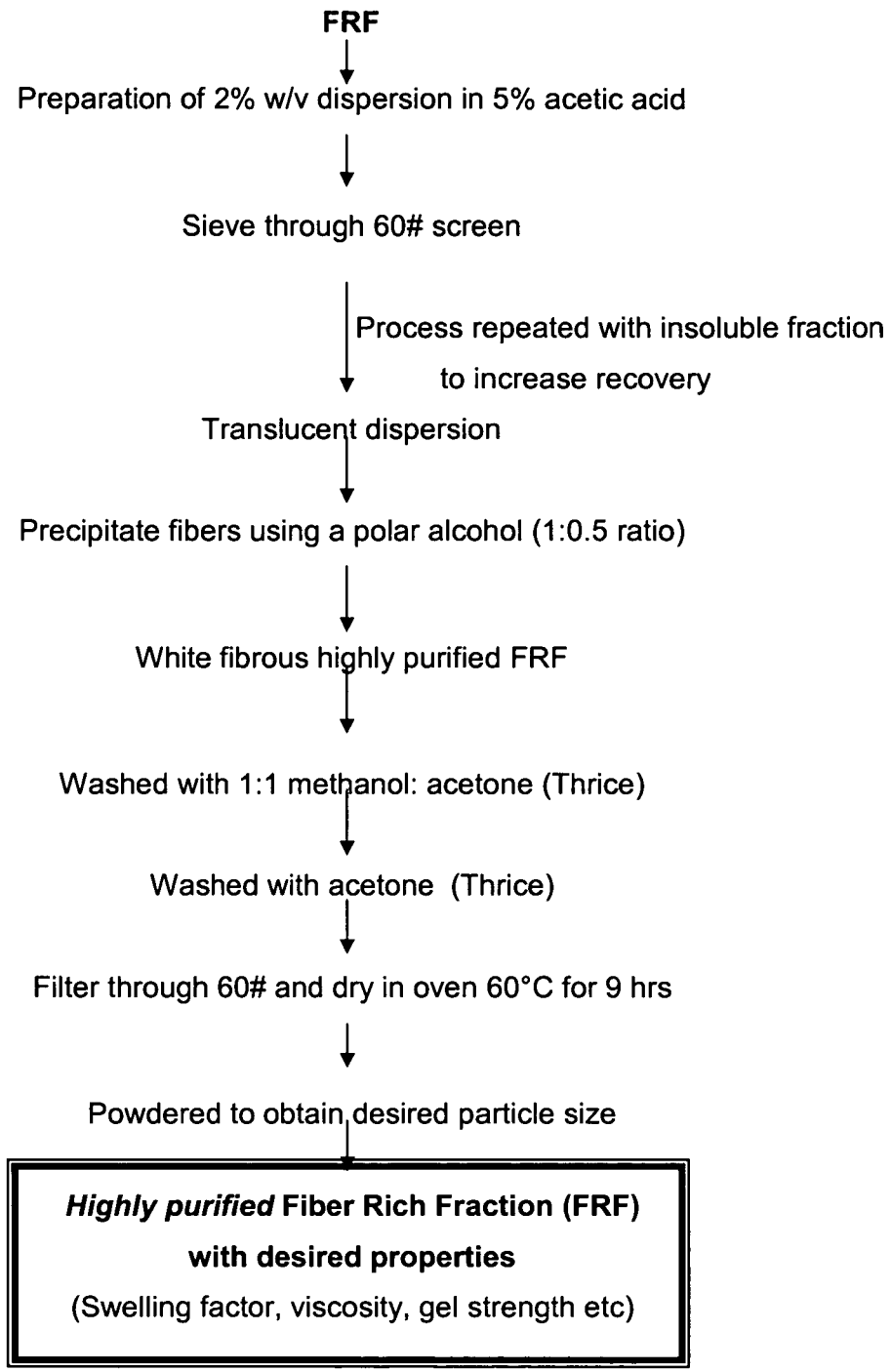
FIG. 3 demonstrates a representative flow chart for the process of purification of fiber rich fraction to obtain a highly purified fiber rich fraction.

Process of Obtaining Highly Purified FRF from FRF:

The preferred embodiment for carrying out the process steps of obtaining highly purified FRF from FRF is illustrated in the flow chart represented by FIG. 3.

The first step is preparation of dispersion of from about 2-5% w/v of FRF in a solvent. The process is carried out at room temperature and ambient atmospheric pressure; however, higher temperatures can be employed if necessary. Solvent used for extraction may be selected from water, 5% glacial acetic acid or any other solvent in which FRF can produce dispersion, this is known to a person skilled in art.

Preferably 5% glacial acetic acid is used for extraction as it results in increased yield and whiter product. The concentration of FRF is only limited by the processability as at higher concentrations due to increased viscosity stirring becomes difficult. The dispersion is then filtered or centrifuged. The insoluble fraction is subjected to further extraction using a solvent for better recovery.

The filtered dispersion is treated with an appropriate volume of a water-miscible, pharmaceutically acceptable solvent, which causes the precipitation of purified FRF. Any of the pharmaceutically acceptable lower alkyl alcohols or ketones are suitable, such as ethanol, methanol, isopropyl alcohol, acetone, and the like can be employed. Methanol is a preferred solvent. While the ratio of the volumes of the water-miscible solvent to the dispersion may vary from about 1 to 5 to 5 to 1, more preferably a ratio of 1:2 is used. To minimize the volume of solvent used, the volume of the dispersion may be reduced by evaporating water before adding the solvent. The resulting hairy fibers are separated from the liquids by any means known to one skilled in the art such as centrifugation or filtration.

Further purification of the white hairy fibers is carried out using any of the process pharmaceutical acceptable lower alkyl alcohols or ketones are suitable, such as ethanol, isopropyl alcohol, acetone, and the like. Preferably 1:1 mixture of absolute ethanol and acetone is used. This step removes the traces of moisture present in the highly purified FRF; thereby aids in drying of the product at lower temperature conditions. Use of acid in the preparation of dispersion results in a product, which is acidic in nature and is not desired for a pharmaceutical excipient and therefore the product is neutralized using alkali solution. Various alkalizing agents used include ethanolic sodium hydroxide solution, sodium bicarbonate solution, calcium hydroxide solution, dilute ammonia etc. These alkalizing agents may be used in solutions having concentration range of 0.1-1M. The product can be further treated with a lower alkyl alcohols or ketones as mentioned above to remove traces of moisture. The resulting highly purified FRF is dried at a temperature less than 100 degrees centigrade for a period of time sufficient to dry the material to moisture content of less than 10%. Drying can be carried out using any of the equipments such as tray dryer, fluidized bed dryer, vacuum dryer etc. The conditions for drying are however very critical as high temperature, humidity and the rate of drying may cause discoloration of the product. Once the dried material is obtained it is further broken up by any means known in the art to provide a suitable particle size.

Analysis of Highly Purified FRF:

Highly purified FRF isolated from process of the instant invention was analyzed using standard AOAC methods and the results are indicated in the table below:

TABLE 3

Characterization of highly purified FRF

| No. | Test | Results |
|---|---|---|
| 1 | Moisture content (AOAC 17th edition 2000, 925.10) | <10% |
| 2 | Total ash (AOAC 17th edition 2000, 923.03) | <5% |
| 3 | Fat (AOAC 17th edition 2000, 984.13) | <5% |
| 4 | Protein (N × 6.25) (AOAC 17th edition 2000, 920.85) | <10% |
| 5 | Dietary fibers (AOAC 17th edition 2000, 991.43) | 50-98% |
|   | Insoluble dietary fiber (ISDF) | 30-80% |
|   | Soluble dietary fiber (SDF) | 15-40% |
|   | ISDF/SDF | >0.8 |
| 6 | Viscosity at 2% w/v Using Brookfield viscometer | >50,000 cps |

The amount of dietary fibers in the highly purified FRF obtained by instant embodiment ranges from 50-98%, preferably 50-95%.

The ratio of insoluble to soluble dietary fiber is greater than 0.8, preferably greater than 1.2 more preferably in between 1.2-3.0. Protein content in the highly purified FRF is not more than 10% preferably not more than 8%.

Both FRF and highly purified FRF have unique properties in terms of dietary fiber content, ratio of insoluble to soluble dietary fiber, low fat and protein content (despite minimum use of solvents and no lipophilic solvents like hexane and chloroform used) and high viscosity.

Due to these features the fiber rich fractions of this invention can be employed as a pharmaceutical excipient.

Drug substances are seldom administered alone, but rather as part of a formulation in combination with one or more non-medical agents that served varied and specialized pharmaceutical function, which are termed as pharmaceutical ingredients or excipients. These pharmaceutical excipients solubilize, suspend, thicken, dilute, emulsify, stabilize, preserve, color, flavor and fashion medicinal agents into efficacious and appealing dosage forms (Remington: The science and practice of Pharmacy, vol 1, pp 868 (2002)).

The word "excipient" as used herein implies non-pharmaceutically active additives used in the manufacture of a pharmaceutical composition, the additive allows the pharmaceutically active ingredient or medicament to be manufactured into a pharmaceutical formulation or a galenic formulation which provides the necessary bioavailability of the medicament to the patient upon the administration of the pharmaceutical composition. The bioavailability of a given dosage form is dependent on process variables and the interrelationship between the various excipients and the active ingredient.

FRF and highly purified FRF are multifunctional excipients and can be used for several applications.

In one embodiment, the excipients of the present invention when used in solid dosage forms, it can serve as, inter alia, a binder. Binders are used to hold together the structure of the dosage forms. The described excipient has the property to bind together all the other ingredients after sufficient compression forces have been applied and provide the physical, structural integrity of the tablets. Tablets can be manufactured using three main processes: wet granulation, dry granulation and direct compression. Both the excipients described herein, namely FRF and highly purified FRF can act both as dry as well as wet binder. They can be used at a concentration ranging from 0.5 to 20% by weight of the total formulation.

In yet another embodiment, the excipients of the invention can be used as disintegrants. When the tablet is used as a pharmaceutical product, in addition to the abovementioned requirement of structural strength, the disintegration time of the tablet must be short enough for the tablet to express its pharmacological effect after the tablet is orally taken. Generally, after administration, tablet is disintegrated in digestive tracts, and then the active pharmaceutical ingredient is dissolved in a digestive liquid. Both FRF and highly purified FRF can be used at a concentration ranging from 0.5 to 20% of the finished dosage form weight. The disintegration properties are based upon the ability of the FRF to swell in the presence of a fluid such as water or gastric juice. This swelling disrupts the physical continuity of the tablet structure, leading to its physical disintegration.

In yet another embodiment, the excipients of the invention can be used as thickening agents.

An important class of oral dosage forms includes syrups, suspensions and emulsions. In these systems the pharmaceutically active ingredient may be dissolved in an aqueous or non-aqueous solvent or combination, by suspending the pharmaceutically active ingredient (if it is insoluble) in an appropriate medium, or by incorporating the pharmaceutical active ingredient into one of the two phases of an oil and water system. One of the important aspects of these dosage forms is the viscosity, which is required to prevent sedimentation rate of the solids in suspension and to achieve desired stability in case of emulsion and to arrive at a consistency suitable for administration in case of solutions. Thickening agents or agents imparting viscosity are therefore an important additive in these formulations. The FRF can be employed as a thickening agent for pharmaceutically active ingredient solutions, suspension or emulsions. FRF can be used at a concentration level from 0.5 to 20% w/v. The actual concentration of FRF can be selected based on the desired consistency.

In yet another embodiment, the excipients of the invention can be used as stabilizers for liquid dosage forms.

An important aspect of disperse systems is the agent that stabilizes the system. This can be the suspending agent or the emulsifying agent. FRFs of the present invention can be used as a suspending agent or as an emulsifying agent at a concentration ranging from 0.5 to 20% w/v. The FRF can be employed as a thickening agent, base or gelling agent for these semisolid formulations. It can be used at a concentration ranging from 0.5-50% w/v. The concentration can be selected based on the desired consistency, appearance and the desired physical and chemical properties of the final product.

In yet another embodiment, the excipients of the invention can be used as coating agents.

Tablets are coated for a number of reasons, including protecting the medicinal agent against destructive exposure to air and/or humidity, mask the taste of the drug, provide special characteristics of drug release and to provide aesthetic or distinction to the product. The FRFs of the instant invention can be employed as a coating agent for coating of various dosage forms. It can be used at a concentration level from about 0.5 to 20% of the finished dosage form weight. The concentration can be selected based on the desired consistency, appearance and the desired physical and chemical properties of the final product. Commonly employed plasticizers such as polyethylene glycol can be also used along with opacifiers and colorants and other excipients.

In yet another embodiment, the excipients of the invention can be used as release retarding polymers.

The goal of any drug delivery system is to provide a therapeutic amount of drug to the proper site in the body to achieve promptly and then maintain the desired drug concentration. The advantages of modified release products are well known in the pharmaceutical field and include the ability to maintain a desired blood level of a medicament over a comparatively longer period of time while increasing patient compliance by reducing the number of administrations necessary to achieve the same. Among all these approaches matrix approach is commonly used, as it is easy to formulate dosage forms at large scale at relatively low costs. This approach involves drug release via diffusion and dissolution. In such systems the rate of dissolution of drug is reduced by, for example, embedding the drug in a polymeric matrix or surrounding it with a polymeric barrier membrane through which drug must diffuse to be released for absorption.

A number of polymers are reported for this purpose including cellulose derivatives. The FRF and highly purified FRF can be employed as a release-retarding polymer for controlling the release of drug from various dosage forms. As a release-retarding polymer, FRF can be used at a concentration level from about 5 to about 95% of the finished dosage form weight. The concentration can be selected based on the desired release profile, and the nature and dose of the active pharmaceutical ingredient. FRFs of the present invention can be used alone or in combination with the said polymers. FRFs can be effectively used for drugs with varying solubilities such as very soluble (1 part in less than 1 part of water) to practically insoluble (1 part in more than 10,000 parts of water). FRFs can thus be used for controlled delivery of both lipophilic and hydrophilic drugs. Also, they can be conveniently employed for large, medium and low dose drugs, alone or in combination. FRF can be incorporated in the various dosage forms that can be used for controlling the drug release such as capsules, tablets, micro granules, pellets, coated systems, etc. In the manufacturing of capsule shell hydrophilic polymers such as Gelatin, HPMC or xanthan gum are employed to provide the flexible nature of the shell. For similar application FRF and highly purified FRF can be employed due to its polymeric and film forming property.

FRF and highly purified FRF can also be employed in the manufacturing of soft gelatin capsules.

In yet another embodiment, the excipients of the invention can be used as structural component in films.

Films or patches are mainly developed for transdermal application as well as application to the mucosal tissues such as oral mucosal, eye, vagina etc. In these systems the drug is distributed within a thin, hydrophilic/hydrophobic adhesive film. Transdermal devices known in the art include reservoir type devices including membranes, pressure-sensitive adhesive matrices and skin patches. The FRFs can be employed as a structural component in a film or patch formulation. As such, FRFs can be used at a concentration level from 0.5 to about 50% w/v. The concentration can be selected based on the desired consistency, appearance and the desired physical and chemical properties of the final product. Mechanical properties of the film are extremely important. These include tensile strength, modulus of elasticity, percent elongation at break, folding endurance water uptake, flatness etc In a further embodiment the FRF can be incorporated in the following dosage forms: a capsule, a tablet, an ovule, a suppository, an insert, a wafer, a chewable tablet, a buccal tablet, a sublingual tablet, a quick-dissolve tablet, an effervescent tablet, a granule, a pellet, a bead, a pill, a sachet, a sprinkle, a film, an ointment, a cream, a gel, a dry syrup, a reconstitutable solid, a suspension, an emulsion, a lozenge, a troche, an implant, a powder, a triturate, a platelet, or a strip. These pharmaceutical compositions can be formulated for immediate release, pulsatile release, controlled release, extended release, modified release, delayed release, targeted release, or targeted delayed release. Also the compositions can be formulated for oral, nasal, ocular, urethral, buccal, transmucosal, vaginal, topical or rectal delivery. For development of these dosage forms this excipient can be combined with other excipients such as water soluble polymer, water insoluble polymers, hydrophobic materials, hydrophilic materials, waxes, disintegrants, superdisintegrants, diluents, binders, etc.

Certain modifications to the present invention as will be apparent to a person skilled in art are not to depart from the scope of the invention and will be encompassed within the scope of the invention. For example, the ratios of FRF to active pharmaceutical ingredient may be varied, as may the nature and number of other excipients used along with the FRF. Similarly, other methods of physical separation of the FRF from the embryo work equivalently to the specific examples taught here may be construed.

The invention and its objects will now be exemplified in terms of non-limiting examples as under:

Example 1

Isolation of FRF from Fenugreek Seeds

5 Kg Fenugreek seeds were purchased from a local source (Mumbai, India). Seeds were introduced into the multimill with a 4 mm sieve and hammer forward operating at fast speed. The material was collected at the end of the first run and passed through a 16# sieve. The under fraction was removed and the fraction retained was again passed through the multimill. The process was repeated for at least 5 more times and yellow embryo content in the mixture was determined by physically separating the two fractions. The embryo content of the fraction was found to be about 54%, which suggested a need to further continue passage through multimill. After another 6 passage through multimill and subsequent sieving through 16# sieve a fraction with only 17% of yellow embryo fraction was reached. This fraction (~1.5 Kg) was then separated by fluidization and sifting through 12# to give fiber rich fraction (~900 gms).

Example 2

Enrichment of Fiber Rich Fraction Content by the Process of the Invention

5 Kg Fenugreek seeds were purchased from a local source (Mumbai, India). Seeds were introduced into the multimill with a 5 mm sieve and hammer forward operating at fast speed. The material was collected at the end of the first run and passed through a 16# sieve. The fraction retained on the sieve was evaluated for the embryo content and Fiber rich fraction content. Similar fractions were also collected after 4, 8 and 12 runs. Finally the Fiber rich fraction was obtained after fluidization and sifting through 12# sieve. The Fiber rich fraction content and the viscosities of these fractions and the isolated FRF were determined.

TABLE 4

Husk content and viscosity achieved after the enrichment process

|  | After 1$^{st}$ run | After 4$^{th}$ run | After 8$^{th}$ run | After 12$^{th}$ run | FRF |
|---|---|---|---|---|---|
| Husk content (%) | 3% | 15% | 40% | 60% | >90% |
| Viscosity* in cps | <2000 | <2000 | <2000 | 10000 | 48000 |

2% w/v solution using Brookfield viscometer.

This data suggests that serial and controlled milling is essential for isolation of fiber rich fraction. This is evident from both the increase in husk content of the fiber rich fraction as well as from the increase in viscosity.

Example 3

Characterization of FRF

Characterization of FRF isolated from two different samples of Fenugreek seeds by a process indicated in example 1 is as follows:

TABLE 5

Characterization of FRF

| No. | Test | Sample I | Sample II |
|---|---|---|---|
| 1 | Moisture content (AOAC 17$^{th}$ edition 2000, 925.10) | 6.46 | 4.25 |
| 2 | Total ash (AOAC 17$^{th}$ edition 2000, 923.03) | 3.05 | 3.5 |
| 3 | Fat (AOAC 17$^{th}$ edition 2000, 984.13) | 1.53 | 0.92 |
| 4 | Protein (N × 6.25) (AOAC 17$^{th}$ edition 2000, 920.85) | 3.95 | 8.93 |
| 5 | Dietary fibers (AOAC 17$^{th}$ edition 2000, 991.43) | | |
| | Insoluble dietary fiber (ISDF) | 40.30 | 33.62 |
| | Soluble dietary fiber (SDF) | 38.00 | 25.22 |
| | ISDF/SDF | 1.06 | 1.33 |
| 6 | Viscosity at 2% w/v Using Brookfield viscometer | 15000 cps | 20000 cps |

The data suggests low protein content as well as high content of dietary fibers with a ratio of insoluble dietary fiber to soluble dietary fiber being greater than 1.0 and a high viscosity suggesting suitability of the isolated FRF as a pharmaceutical excipient.

Example 4

Determination of Amount of Embryo Present in FRF

Fenugreek is grown in various parts of India and as with any natural product geographical variations are possible with Fenugreek seeds. These geographical variations may lead to difference in the properties of the isolated FRF. To understand the variability associated with fenugreek seeds and its effect on the properties of FRF, FRF was isolated from 4 different samples of fenugreek seeds.

The process of the present invention is a simple sequential physical separation, which means that some amount of yellow embryo will always contaminate the final product and therefore keeping this yellow embryo fraction at minimum level is very important. This example shows determination of the yellow embryo fraction of FRF isolated by process of present invention. 10 gm of the FRF was taken and the yellow embryo fraction was physically separated from the FRF and weighed.

TABLE 6

Result showing the embryo content in the FRF

|  | Sample 1 | Sample 2 | Sample 3 | Sample 4 |
|---|---|---|---|---|
| FRF taken (gms) | 10.0 | 10.0 | 10.0 | 10.0 |
| Yellow embryo (gms) | 0.344 | 0.42 | 0.48 | 0.13 |
| % of the embryo in the FRF | 3.44 | 4.2 | 4.8 | 1.3 |

The above data suggest that for all different FRF the amount of yellow embryo was less than 5% as desired for FRF to be used as a pharmaceutical excipient.

Example 5

Purification of FRF to Obtain Highly Purified FRF

Dispersion of FRF was prepared by adding about 250 gms of FRF to 12.5 L of 5% glacial acetic acid under stirring for 1 hr. The dispersion thus obtained was filtered through a 60# sieve to separate the dispersion from insoluble mass. The water insoluble fraction was again subjected to extraction for better recovery. All fractions were combined to give a volume of about 35 L. The dispersion thus obtained was treated with approximately half the quantity of isopropyl alcohol (~18 L), which resulted in the precipitation of FRF. Thus obtained white hairy mass was filtered. This highly purified FRF contains large amounts of water bound to it and if this water is not removed, it affects the properties of the final product as well as causes difficulty in drying the mass to obtain a powder. Traces of moisture were removed by treating the fibers with a 1 L of 1:1 mixture of absolute ethanol and acetone and filtered through 60#. This treatment was given thrice. Neutralization of the fibrous mass along with ethanol-acetone solvent mixture was carried out using 0.1M ethanolic sodium hydroxide. pH was adjusted between 6-7.5. Final washing of the product was given with acetone. The highly purified FRF thus obtained was dried at 60 degrees centigrade for 9 hrs to obtain dried fibers of highly purified FRF, which was powdered to obtain a 60# fraction. The highly purified FRF can be used for various applications in pharmaceutical, cosmetic, food and textile industry etc.

Example 6

Characterization of Highly Purified FRF

Characterization of highly purified FRF isolated from two different sample of Fenugreek seeds by a process indicated in example 4 is as follows:

TABLE 7

Characterization of highly purified FRF

| No. | Test | Sample I | Sample II |
|---|---|---|---|
| 1 | Moisture content (AOAC 17$^{th}$ edition 2000, 925.10) | 7.62 | 7.62 |
| 2 | Total ash (AOAC 17$^{th}$ edition 2000, 923.03) | 0.60 | 0.67 |
| 3 | Fat (AOAC 17$^{th}$ edition 2000, 984.13) | 0.16 | 1.18 |
| 4 | Protein (N × 6.25) (AOAC 17$^{th}$ edition 2000, 920.85) | 4.90 | 1.73 |
| 5 | Dietary fibers (AOAC 17$^{th}$ edition 2000, 991.43) |  |  |
|  | Insoluble dietary fiber (ISDF) | 63.40 | 60.10 |
|  | Soluble dietary fiber (SDF) | 32.10 | 21.60 |
|  | ISDF/SDF | 1.98 | 2.78 |
| 6 | Viscosity at 2% w/v Using Brookfield viscometer | 70,000 cps | 95,000 cps |

The data demonstrates low protein and fat content as well as very high content of dietary fibers with a ratio of insoluble dietary fiber to soluble dietary fiber being greater than 1.1. The viscosity of greater than 50,000 at 2% concentration suggests that highly purified FRF is an ideal excipient for controlled drug delivery systems.

Example 7

Comparative Data of the Soluble and Insoluble Dietary Fiber Content of Reported Fenugreek Dietary Fibers and FRF and Highly Purified FRF Several products containing high proportion of dietary fibers are available in the market. The following table 8 shows the comparative data on the fiber content of various products obtained from their websites versus the same for FRF and highly purified FRF.

TABLE 8

Comparitive data of commercial fenugreek dietary fiber versus FRF and highly purified FRF

|  | Soluble dietary fiber (SDF) (%) | Insoluble dietary fiber (ISDF) (%) | Total dietary fiber (%) | ISDF/SDF |
|---|---|---|---|---|
| Fenulife fiber ® | >50 | <15 | >70 | 0.30 |
| Fenulife extract ® | >65 | <15 | >85 | 0.23 |
| Trifena enriched ® | >65 | <15 | >85 | 0.23 |
| Trifena standard ® | 36 | 24 | >60 | 0.67 |
| FRF | 28 | 43 | >70 | 1.53 |
| Highly purified FRF | 32 | 63 | >90 | 1.96 |

This data clearly distinguishes the FRF and highly purified FRF obtained by process of present invention from the commercially available products in the market that contain greater amount of soluble dietary fibers obtained from Fenugreek seeds.

Example 8

Comparative Data of the Viscosities of Reported Polymers and FRF and Highly Purified FRF The polymers studied were Hydroxypropyl methylcellulose Methocel K100M® and Methocel K4M® (Dow chemicals, Mumbai, India) a well known and well standardized product used frequently in controlled release dosage forms, guar gum and locust bean gum (Lucid colloids, Mumbai, India), both containing galactomannans and FRF and highly purified FRF obtained with the process of present invention. 2% w/v solution of these polymers was prepared in distilled water and kept overnight for deaeration. The viscosities were determined at 25 degrees using Brookfield viscometer with LVT model using spindle No. 4 at 1.5 rpm and are indicated below in Table V:

TABLE 9

Comparitive data of the viscosities of commercially available polymers versus FRF and highly purified FRF

| No. | Polymers | Viscosity in cps |
|---|---|---|
| 1 | Methocel K100M | 101000 |
| 2 | Methocel K4M | 4000 |
| 2 | Guar gum | 2,00,000 |
| 3 | Locust bean gum | 2000 |
| 4 | FRF | 45,000 |
| 5 | Highly purified FRF | 2,44,000 |
| 6 | Fenugreek seeds | 2000 |

This data suggests that highly purified FRF exhibited maximum viscosity compared to all other gums and FRF exhibited a viscosity greater than locust bean gum and Methocel K4M. Thus both FRF and highly purified FRF can act as an effective controlled release excipient.

Fenugreek seeds themselves have a low viscosity when crushed entirely thus demonstrating the importance of serial milling and isolating the fiber rich fraction and further purification to highly purified fiber rich fraction. Also due to its apparent low viscosity, until now, fenugreek seeds have not been considered to be useful as a pharmaceutical excipient.

Example 9

Use of the FRF and Highly Purified FRF as a Controlled Release Vehicle for a Highly Water Soluble Drug-Metformin Hydrochloride The following compositions were prepared to demonstrate the effective use of FRF and highly purified FRF as a controlled release vehicle for a highly water-soluble drug represented by metformin hydrochloride.

TABLE 10

Composition of controlled release metformin tablets

| Ingredients | Lot A (mg/unit) | Lot B (mg/unit) | Lot C (mg/unit) |
|---|---|---|---|
| Metformin HCl | 500 | 500 | 500 |
| Kollidone 90F | 25 | — | — |
| Plasdone K30 | — | 25 | 25 |
| METHOCEL ® K100M | 290 | — | — |
| Fiber rich fraction | — | 360 | — |
| Highly purified FRF | — | — | 250 |
| Sodium Carboxymethyl cellulose | 100 | 100 | 100 |
| Methocel E5 Premium LV | 70 | — | — |
| Avicel PH 102 | 10 | 10 | 10 |
| Magnesium stearate | 5 | 5 | 5 |

Metformin was granulated and the granules divided into three lots. Lot A granules were lubricated with METHOCEL® and sodium carboxymethyl cellulose and compressed tablets after lubrication with magnesium stearate. METHOCEL® brand cellulose ethers, commercially available from the Dow Chemical Company, (Mumbai, India) are water-soluble methylcellulose and hydroxypropyl methylcellulose polymers that bind, retain water, thicken, form films, lubricate, and add unique physical properties to various preparations. Lot B granules were lubricated with Fiber rich fraction and sodium carboxymethyl cellulose and compressed into tablets after lubrication with magnesium stearate. Lot C granules were lubricated with highly purified FRF and sodium carboxymethyl cellulose and compressed into tablets after lubrication with magnesium stearate. Dissolution was carried out using 900 ml 6.8 phosphate buffer in USP apparatus I (Basket).

Figure 4:
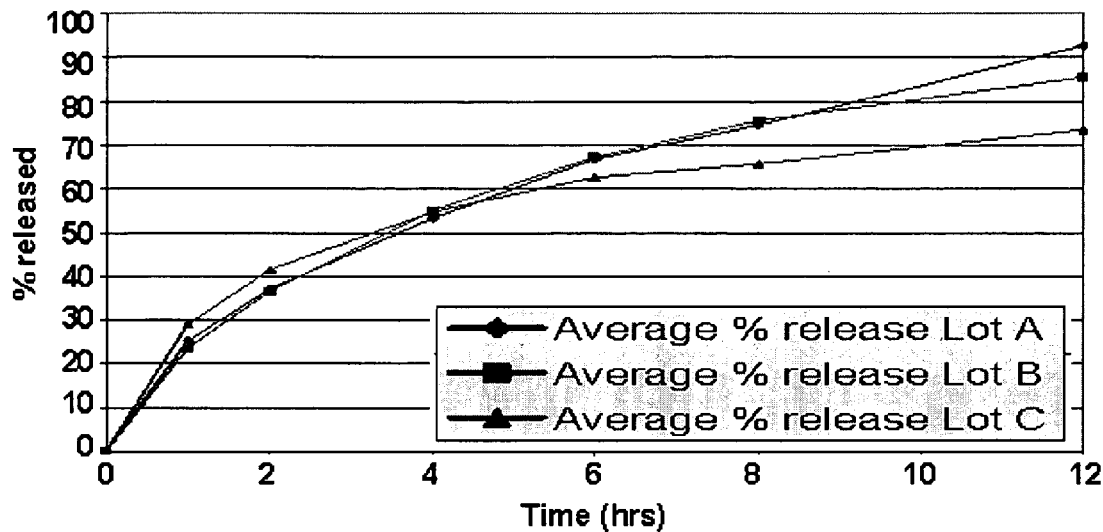
FIG. 4 illustrates the comparative dissolution profiles of metformin hydrochloride from HPMC, FRF and highly purified FRF matrix.

The dissolution profile is as indicated in the table VI below along with a graphical representation as seen in FIG. 4.

TABLE 11

Dissolution profile of Lots A, B and C at various time intervels

| Time intervals (hrs) | Average % release | | |
|---|---|---|---|
| | Lot A | Lot B | Lot C |
| 1 | 25.24 | 23.64 | 29.01 |
| 2 | 37.18 | 36.66 | 41.60 |
| 4 | 53.32 | 55.12 | 54.79 |
| 6 | 66.82 | 67.23 | 62.65 |
| 8 | 74.64 | 75.74 | 65.80 |
| 12 | 92.70 | 82.51 | 73.59 |

The following conclusions can be drawn from the above data:

Both FRF and highly purified FRF can be used as a sustained release excipient for highly water-soluble drug such as metformin hydrochloride.

The Fiber rich fraction can act as a controlled release vehicle at a concentration equivalent to METHOCEL® concentrations.

Highly purified FRF is a better release retardant compared to HPMC as it is employed at a concentration of 25% w/w compared to 36% w/w of HPMC and still tablets prepared with highly purified FRF released only 74% of the drug at the end of 12 hrs compared to 93% in case of HPMC.

Example 10

Use of the FRF and Highly Purified FRF Alone as a Controlled Release Vehicle for a Highly Water Soluble Drug-Metformin Hydrochloride In the previous example FRF and highly purified FRF were employed as controlled release excipients in combination with sodium carboxymethyl cellulose. In this example both FRF and highly purified FRF are employed alone as controlled release vehicle for a highly water-soluble drug-metformin hydrochloride:

TABLE 12

Composition of controlled release metformin tablets

| Ingredients | Lot A (mg/unit) | Lot B (mg/unit) |
|---|---|---|
| Metformin HCl | 500 | 500 |
| Kollidone 90F | 25 | 25 |
| Fiber rich fraction | 360 | — |
| Highly purified FRF | — | 250 |
| Dicalcium phosphate | 100 | 100 |
| Avicel PH 102 | 10 | 10 |
| Magnesium stearate | 5 | 5 |

Metformin hydrochloride was granulated and the granules divided into two lots. Lot A granules were lubricated with Fiber rich fraction and compressed into tablets after lubrication with magnesium stearate. Lot B granules were lubricated with Highly purified FRF and compressed into tablets after lubrication with magnesium stearate. Dissolution was carried out using 900 ml 6.8 phosphate buffer in USP apparatus I (Basket).

Figure 5:
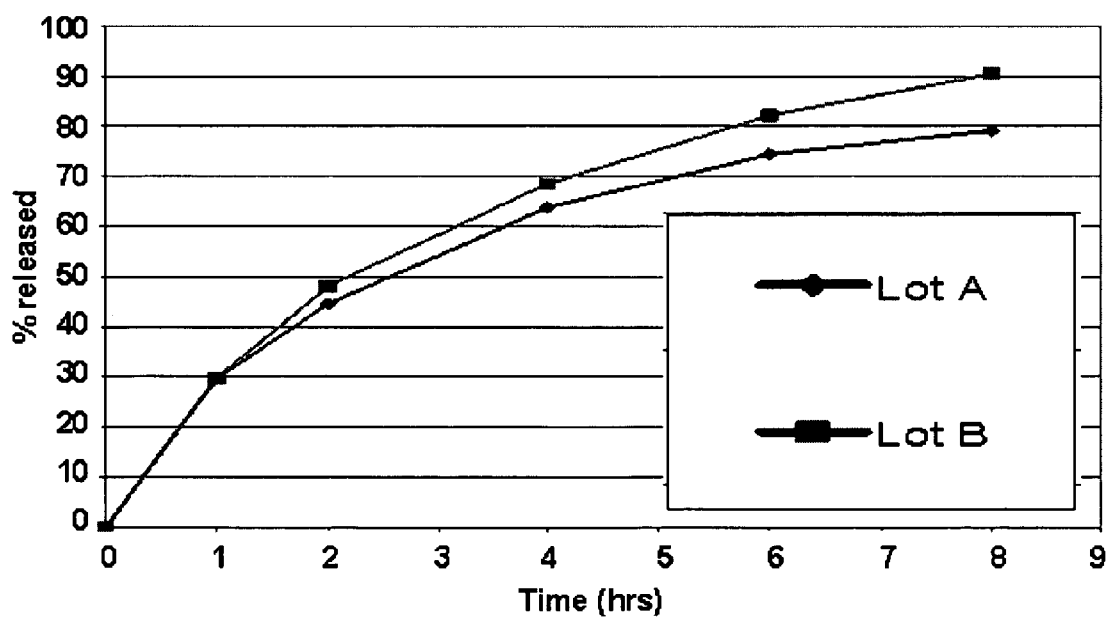
FIG. 5 illustrates the dissolution profiles of metformin hydrochloride from FRF and highly purified FRF matrix.

The dissolution profile is as indicated in the table VII below along with a graphical representation as seen in FIG. 5.

TABLE 13

Dissolution profile of Lots A and B at various time intervals

| Time intervals | Average % release | |
|---|---|---|
| (hrs) | Lot A | Lot B |
| 1 | 29.70 | 29.78 |
| 2 | 44.55 | 48.12 |
| 4 | 63.72 | 68.50 |
| 6 | 74.47 | 82.22 |
| 8 | 79.15 | 90.48 |

It can thus be concluded from the above data that both FRF and highly purified FRF can be used alone as a sustained release excipient for highly water-soluble drug such as metformin hydrochloride.

Example 11

Use of the FRF as a Disintegrating Agent

The fiber rich fraction was incorporated in citalopram tablets and compared with tablets without this excipient.

TABLE 14

Comparison of citalopram tablets with and without FRF

| Excipients | Lot A (mg/tablet) | Lot B (mg/tablet) |
|---|---|---|
| Citalopram hydrobromide | 49.96 | 49.96 |
| Microcrystalline cellulose | 120.00 | 112.00 |
| Lactose | 184.04 | 184.04 |
| Pregelatinised starch | 30.00 | 30.00 |
| Fiber rich fraction | — | 8.00 |
| Magnesium stearate | 4.00 | 4.00 |
| Tablet weight (mg) | 388.00 | 388.00 |
| Hardness (Kg/cm$^2$) | 7-8 | 7-8 |
| Disintegration time (min.) | >10 min | 7-8 |

Citalopram hydrobromide tablets were prepared using the Fiber Rich Fraction as a disintegrant. A control was also prepared without the excipient and disintegration time was recorded using Electrolab disintegration test apparatus.

The formulation containing the Fiber rich fraction (Lot B) exhibited a disintegration time of 7-8 min whereas for tablets without this excipient (Lot A) exhibited a disintegration time of greater than 10 min. which suggest that the Fiber rich fraction can be used as a disintegrating agent for tablets and capsules.

Example 12

Use of the FRF as a Binder

Binding properties of the Fiber rich fraction was studied in this experiment. In Lot A the pharmaceutical excipient FRF was dry mixed with the drug and other formulation excipients and the blend was granulated using water. In Lot B the FRF was dispersed in water and this solution was then used for granulation of the blend.

TABLE 15

Composition of simvastatin tablets using FRF as binder

| Ingredients | Lot A (mg/tablet) | Lot B (mg/tablet) |
|---|---|---|
| Simvastatin | 40.00 | 40.00 |
| Microcrystalline cellulose | 250.96 | 260.96 |
| Lactose | 75.00 | 75.00 |
| Fiber rich traction | 20.00 | 10.00 |
| Magnesium stearate | 2.00 | 2.00 |
| Butylated hydroxy anisole | 0.04 | 0.04 |
| Tablet weight (mg) | 388.00 | 388.00 |
| % fines (−100 #) | 8.69 | |
| % compressibility | 16.29 | 18.74 |
| Hardness (Kg/cm$^2$) | 6-7 | 7-8 |
| Disintegration time (min.) | 5-6 | 3-4 |

Thus it can be seen from the above table that the pharmaceutical excipient FRF has good binding property. This is evident from the hardness achieved, % fines obtained in the granules and the compressibility of the blend.

Example 13

Use of the Excipient Highly Purified FRF as a Thickening Agent

Owing to high swelling properties, highly purified FRF can be used effectively in the preparation of gels, ointments creams etc. The following example demonstrates the use of the highly purified FRF as a thickening agent in Miconazole gel.

TABLE 16

Composition of miconazole gel

| Ingredients | Gm/batch |
|---|---|
| Miconazole | 2.00 |
| Tween 20 | 0.50 |
| Glycerol | 70.00 |
| Sodium saccharin | 0.20 |
| Highly purified FRF | 2.00 |
| Demineralised water | 25.30 |

Highly purified FRF was dispersed in glycerol and gel was prepared by hydrating highly purified FRF. A solution of tween 20 and sodium saccharin in demineralised water was further added and homogenized thoroughly.

The gel thus obtained had good consistency, good extrudability and spreadability. Thus this excipient can be used as a thickening or gelling agent.

Example 14

Use of the Highly Purified FRF as a Film-Forming Agent

Apart from swelling properties of the excipient highly purified FRF has its ability to form free as well as medicated film was evaluated. The following composition was prepared:

TABLE 17

Composition of Diclofenac film formulation

| Ingredients | Gm/batch |
|---|---|
| Diclofenac diethylamine | 1.00 |
| Propylene glycol | 0.25 |
| Fiber rich fraction | 1.00 |
| Distilled water (q.s.) | 100 |

Highly purified FRF was dispersed in distilled water sifted through 80 #. To this sifted solution diclofenac diethylamine previously dispersed in propylene glycol was added. The resulting solution was poured in siliconised petridishes and dried in a tray drier at 60 degrees centigrade for about 8-12 hours. The resulting film had desired elasticity, flatness, and tensile strength. Thus the excipient can be used for the preparation of films that might be employed for transdermal or buccal or any other application.

Example 15

Use of Highly Purified FRF as a Coating Agent

As highly purified FRF has good film forming properties, it should be readily used as a coating agent for film coating of tablets. The following composition was used for the preparation of film coating solution.

TABLE 18

Composition of film coating solution

| Ingredients | Gm/batch |
|---|---|
| Highly purified FRF | 2.25 |
| Propylene glycol | 9.00 |
| Talc | 13.50 |
| Titanium dioxide | 13.50 |
| Quinoline yellow lake | 1.13 |
| Distilled water | 272.6 |

Highly purified FRF was dispersed in distilled water and propylene glycol. Talc and titanium dioxide were added to this dispersion. Finally quinoline yellow lake was added and the solution was passed through 80 # sieve. The resulting solution was employed for coating of placebo tablets. Samples were removed at different levels of coating. Coating was completely smooth and the defects such as logo bridging, orange peel effect, etc were not observed. Formation of a uniform coat suggested the application of excipient as a coating agent.

Example 16

Use of the FRF as a Suspending Agent

The following composition was made to demonstrate the use of FRF as a suspending agent:

TABLE 19

Composition of calcium suspension

| Ingredients | Qty/I00 ml |
|---|---|
| Sugar syrup | 50.20 |
| Calcium carbonate | 12.70 |
| Sorbitol | 10.00 |
| Glycerin | 10.00 |
| Fiber rich fraction | 3.00 |
| Erythrosine solution (2%) | 0.10 |
| Raspberry flavor | 0.10 |
| D.M. water | q.s |

The FRF was used as a suspending agent at a concentration of 3% in a high dose calcium suspension. Viscosity of the solution was determined using Brookfield viscometer and was found to be about 2000 cps at 25 degrees centigrade. The sedimentation rate of the formulation was determined over a period of 30 days under ambient conditions and almost no sedimentation was observed. The pharmaceutical excipient described in the instant invention can thus be used effectively as a suspending agent.

Example 17

Use of the FRF in Shampoo Containing Herbal Extracts

The following composition was made to demonstrate the use of FRF in Shampoo containing herbal extracts.

TABLE 20

Composition of shampoo containing FRF

| Ingredients | Quantity (% w/w) |
|---|---|
| SSC-200 base | 53.57 |
| Herbal extract | 2.00 |
| Formalin | 0.10 |
| Silicon oil | 3.00 |
| Fiber Rich Fraction | 5.00 |
| pH adjusting agent (dil. HCl or NaOH) | q.s. |
| Color | 1.02 |
| Perfume | 1.00 |
| Purified water | q.s. |

The aqueous dispersion of FRF was added into the SSC-200 base. To this mixture herbal extract was incorporated under constant stirring. Then formalin and perfume were added to the mixture, and the pH was adjusted to 6-7. Finally silicon oil emulsion was added and stirred to get a homogenous shampoo. The required amount of color was added in the form of aqueous solution and the weight is adjusted with water. The shampoo thus obtained was evaluated for viscosity, wettability, pH and other parameters.

The formulated shampoo using FRF exhibited the desired properties in terms of viscosity and it was stable over a period of time.

What is claimed is:

1. A fiber rich fraction from *Trigonella Foenum-graceum* containing:
   dietary fibers from 50% by weight to 80% by weight of the total weight of the fiber rich fraction, wherein said dietary fibers have a ratio of insoluble to soluble dietary fiber greater than 0.8;
   an insoluble dietary fiber content greater than 28% by weight of the total weight of the fiber rich fraction; and
   a protein content of less than 5% by weight of the total weight of the fiber rich fraction;
   wherein said fiber rich fraction has a viscosity greater than 10000 centipoise (cps) at 2% w/v concentration at 25° C.

2. The fiber rich fraction according to claim 1, wherein the dietary fibers range from 50% by weight to 75% by weight of the total weight of the fiber rich fraction, the ratio of insoluble to soluble dietary fiber is 1.2-3.0, and the insoluble dietary fiber content is greater than 30% by weight of the total weight of the fiber rich fraction.

3. A purified fiber rich fraction from *Trigonella Foenum-graceum*, comprising:
   dietary fibers from 50% by weight to 98% by weight of the total weight of the purified fiber rich fraction, wherein said dietary fibers have a ratio of insoluble to soluble dietary fiber greater than 0.8;
   an insoluble dietary fiber content greater than 30% by weight of the total weight of the purified fiber rich fraction; and
   a protein content of less than 5% by weight of the total weight of the purified fiber rich fraction;
   wherein said purified fiber rich fraction has a viscosity greater than 50000 centpoise (cps) at 2% w/v concentration at 25° C.

4. The purified fiber rich fraction according to claim 3 wherein the dietary fibers range from 50% by weight to 95% by weight of the total weight of the purified fiber rich fraction, the ratio of insoluble to soluble dietary fiber is 1.2-3.0, and said insoluble dietary fiber content is greater than 32% by weight of the total weight of the purified fiber rich fraction.

5. A pharmaceutical composition comprising (a) an active pharmaceutical ingredient and (b) a fiber rich fraction as an excipient obtained from *Trigonella foenum-graceum* comprising: dietary fibers from 50% by weight to 80% by weight of the total weight of the fiber rich fraction, wherein said dietary fibers have a ratio of insoluble to soluble dietary fiber greater than 0.8;
   an insoluble dietary fiber content greater than 28% by weight of the total weight of the fiber rich fraction;
   a protein content of less than 5% by weight of the total weight of the fiber rich fraction; and
   wherein said fiber rich fraction has a viscosity greater than 10000 centipoise (cps) at 2% w/v concentration at 25° C.

6. A pharmaceutical composition comprising (a) an active pharmaceutical ingredient and (b) a fiber rich fraction as an excipient obtained from *Trigonella foenum-graceum* comprising: dietary fibers from 50% by weight to 98% by weight of the total weight of the fiber rich fraction, wherein said dietary fibers have a ratio of insoluble to soluble dietary fiber greater than 0.8;
   an insoluble dietary fiber content greater than 30% by weight of the total weight of the fiber rich fraction;
   a protein content of less than 5% by weight of the total weight of the fiber rich fraction; and
   wherein said fiber rich fraction has a viscosity greater than 50000 centipoise (cps) at 2% w/v concentration at 25° C.

7. A method of administering an active pharmaceutical ingredient to a patient comprising orally administering to the patient a pharmaceutical composition of claim 5.

8. A method of administering an active pharmaceutical ingredient to a patient comprising orally administering to the patient a pharmaceutical composition of claim 6.

* * * * *